United States Patent [19]
Kebabian

[11] Patent Number: 5,567,947
[45] Date of Patent: Oct. 22, 1996

[54] SPECTRAL LINE DISCRIMINATOR FOR PASSIVE DETECTION OF FLUORESCENCE

[75] Inventor: Paul L. Kebabian, Acton, Mass.

[73] Assignee: Aerodyne Research, Inc., Billerica, Mass.

[21] Appl. No.: 456,760

[22] Filed: Jun. 1, 1995

[51] Int. Cl.⁶ .................................................. G01N 21/64
[52] U.S. Cl. .................... 250/458.1; 250/459.1
[58] Field of Search ............................ 250/458.1, 459.1, 250/461.1, 361 R

[56] References Cited

U.S. PATENT DOCUMENTS

| | | |
|---|---|---|
| 3,598,994 | 8/1971 | Markle . |
| 3,641,344 | 4/1972 | Markle . |
| 3,769,516 | 10/1973 | Markle et al. . |
| 4,084,905 | 4/1978 | Schreiber et al. ............. 250/458.1 |
| 4,433,245 | 2/1984 | Poultney ....................... 250/458.1 |
| 4,650,336 | 3/1987 | Moll ............................. 250/458.1 |
| 4,671,662 | 6/1987 | Zupanick et al. ............. 250/458.1 |
| 4,708,475 | 11/1987 | Watson ......................... 250/458.1 |
| 4,724,326 | 2/1988 | Poultney et al. ............. 250/458.1 |
| 4,804,849 | 2/1989 | Booth ........................... 250/459.1 |
| 4,804,850 | 2/1989 | Norrish et al. ................ 250/459.1 |
| 4,865,424 | 6/1989 | Zupanick et al. . |
| 4,988,196 | 1/1991 | Gilligan ....................... 250/458.1 |
| 5,014,225 | 5/1991 | Vidaver et al. ............... 250/461.2 |
| 5,130,545 | 7/1992 | Lussier ........................ 250/458.1 |

OTHER PUBLICATIONS

Article, J. C. McFarlane, et al., Plant stress detection by remote measurement of fluorescence, Oct. 1980/vol. 19, No. 19/Applied Optics, pp. 3287–3289.

*Primary Examiner*—Carolyn E. Fields
*Attorney, Agent, or Firm*—Cesari and McKenna

[57] ABSTRACT

A method and apparatus for detecting fluorescence from sunlit plants is based on spectral line discrimination using the A-band and B-band absorption of atmospheric oxygen. Light from a plant including scattered sunlight and the fluorescence from chlorophyll is passed through a chopper into a cell containing low-pressure, high-purity oxygen. A-band or B-band wavelengths present in the light are absorbed by the oxygen in the cell. When the chopper is closed, the absorbed light is remitted as fluorescence into a detector. The intensity of the fluorescence from the oxygen is proportional to the intensity of fluorescence from the plant.

30 Claims, 1 Drawing Sheet

SPECTRAL LINE DISCRIMINATOR FOR PASSIVE DETECTION OF FLUORESCENCE

This invention was made with government support under NSF grant III-9160487 and NASA contract no. NAS 13-665. The government has certain rights in this invention.

FIELD OF THE INVENTION

This invention relates to detection of fluorescence from sunlit targets. More particularly, this invention relates to the use of spectral line discrimination in the passive detection of fluorescence from chlorophyll in plants.

BACKGROUND OF THE INVENTION

In response to excitation by sunlight, chlorophyll in plants fluoresces at wavelengths from about 660 nm to 800 nm. This behavior can be exploited for remote monitoring of the health of plants. For example, the fluorescence intensity from a plant increases when the plant lacks adequate water. Thus, fluorescence intensity data is useful, for instance, in making decisions concerning allocation of irrigation resources.

Discrimination between a signal emitted by a sunlit target and sunlight of the same wavelengths scattered from the target surface is one difficulty in detecting fluorescence from plants. One approach to differentiating the plant signal is spectral line discrimination. A spectral line discriminator observes light from a narrow range of wavelengths in which one or more absorption lines exist in the solar spectrum. (These absorption lines in the solar spectrum are known as Fraunhofer lines, and thus the terms "spectral line discriminator" and "Fraunhofer line discriminator" are used interchangeably in the literature in this field. The lines may result from either atomic species in the sun's atmosphere or from molecular species in the earth's atmosphere.) Specifically, if such a line is fully opaque, that is, having negligible spectral intensity of sunlight at its center, the signal observed at the line center consists entirely of fluorescence from the target, even if at nearby wavelengths outside the absorption line the intensity of the scattered sunlight is much larger than that of the fluorescence.

One such spectral line discriminator detects signals at the center of the line at 656.3 nm due to absorption by atomic hydrogen in the solar atmosphere. This approach is deficient in three respects. First, the intensity of the chlorophyll fluorescence at 656.3 nm is very weak. Second, the absorption line is not fully opaque at its center. These two factors in combination limit the sensitivity attainable with this method. Finally, the narrowband filter required to observe the line center is realized as a Fabry-Perot cavity. This is an expensive component requiring great precision in manufacture.

DESCRIPTION OF THE INVENTION

Brief Summary of the Invention

The present invention overcomes the limitations of prior art methods of detecting fluorescence from sunlit targets, particularly from chlorophyll in the leaves of plants, by taking advantage of absorption by oxygen. Atmospheric oxygen strongly attenuates sunlight incident to the earth's surface at the centers of two groups of narrow spectral lines at wavelengths around 760 nm and 680 nm. These two groups are known, respectively, as the A-band and B-band. Each of these bands consists of about forty lines with substantially opaque centers, as well as weaker lines. Chlorophyll fluoresces strongly at wavelengths in the vicinity of these bands. When light collected from the target is analyzed, any component detected at wavelengths corresponding to the lines of these bands can therefore be attributed almost entirely to chlorophyll fluorescence. The coincidence of the opacity of the oxygen absorption and the strength of the chlorophyll fluorescence at these wavelengths thus averts obscuration of the signal by scattered sunlight.

Spectral line discrimination, allowing differentiation of the signal of interest from scattered sunlight of other wavelengths, is achieved in the following manner. Light from the plant surface is filtered to pass a range of wavelengths in the vicinity of the A-band or B-band and then passes through an optical chopper and into a cavity housing a cell containing low-pressure, high-purity oxygen gas. The oxygen selectively absorbs light at the centers of the oxygen absorption lines of the selected band. While the chopper is closed, the oxygen reemits to a detector some of the absorbed light as fluorescence at the A-band wavelengths. The intensity of this fluorescence is proportional to the fluorescent energy received from the plant.

Because the fluorescence is detected while entrance of light into the cavity is obstructed by the chopper, no selectivity on the part of the detector is required to distinguish the fluorescence by the oxygen in the cavity from the much stronger scattered sunlight passed by the relatively broadband filter. A conventional detector such as a photomultiplier tube can therefore be used. The width of the absorption lines of the oxygen in the cell defines the effective spectral resolution of the present spectral line discriminator. Since the oxygen in the cell is at low pressure, the width of its lines is essentially the Doppler width. This resolution is achieved simultaneously at the center of each of the lines in the selected band. Not only is this resolution higher than can be achieved by conventional means such as a Fabry-Perot cavity, but it is achieved without any critical optical or mechanical parts. Also, unlike the Fabry-Perot, it is not sensitive to the mechanical alignment of the cavity with respect to entering light.

BRIEF DESCRIPTION OF THE DRAWING

The foregoing discussion will be understood more readily from the following detailed description of the invention, when taken in conjunction with the accompanying drawing, in which.

DETAILED DESCRIPTION OF THE INVENTION

Figure 1:
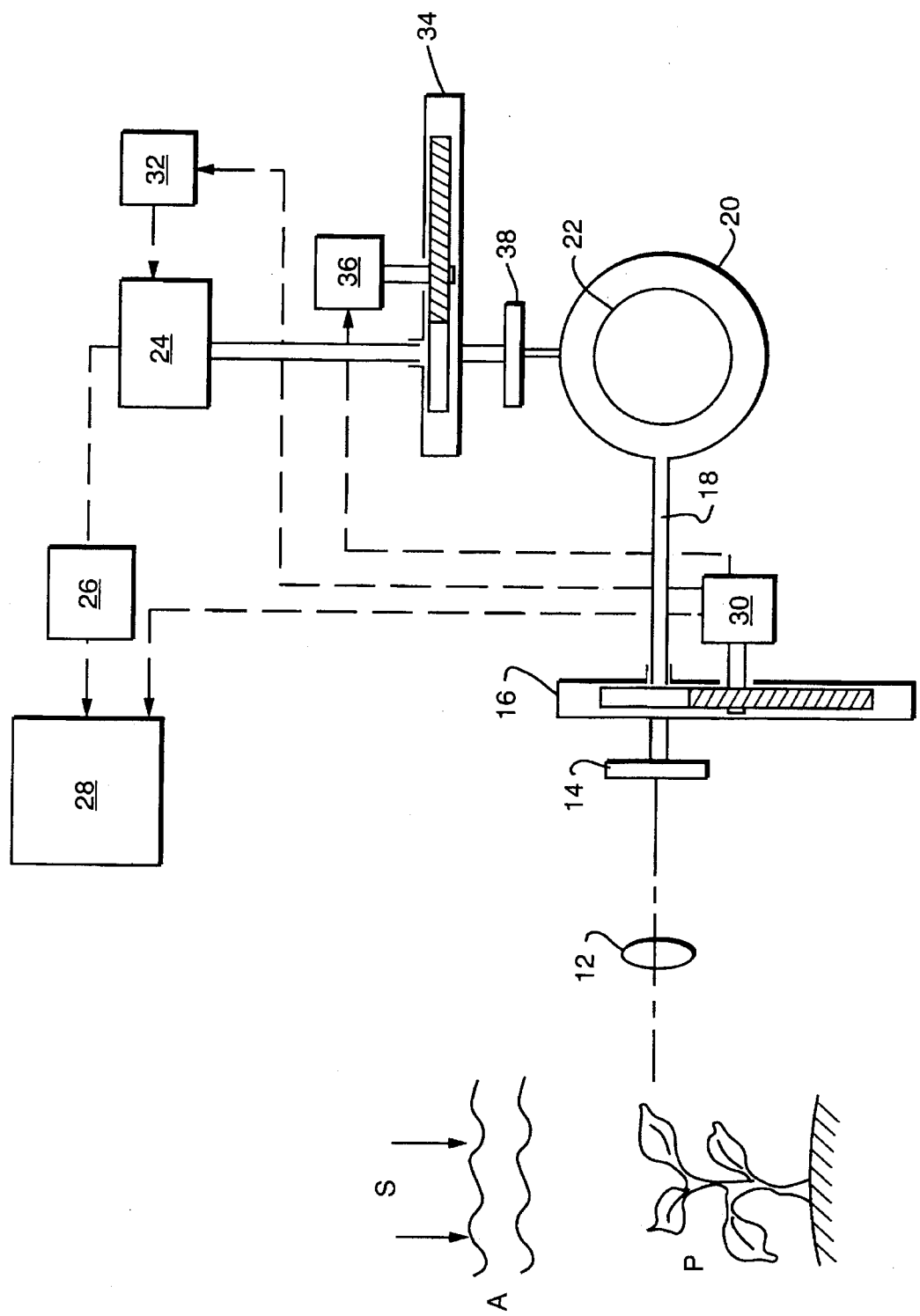
FIG. 1 depicts a method and apparatus for measuring fluorescence from plants.

FIG. 1 illustrates the detection of fluorescence from chlorophyll in plants according to the present invention. As sunlight S travels to the earth's surface, some of its spectral components are absorbed by components of the atmosphere A. In particular, atmospheric oxygen absorbs sunlight at the A-band and B-band located at about 760 nm and 680 nm, respectively. A target on the planet surface, such as a plant P, illuminated by the sunlight absorbs and scatters spectral components of the incident sunlight. After absorbing incident sunlight, chlorophyll in the plant fluoresces at wavelengths from about 660 to 800 nm. Light comprising fluorescence emitted by the plant and sunlight scattered by the plant surface is collected by a collecting lens 12. A plastic Fresnel lens of 4" diameter has been used in this invention.

The collected light is focused by lens 12 through a bandpass filter 14 having a bandwidth of about 10 nm in the A-band or B-band. The light is chopped by an optical chopper 16 and then focused into a light pipe 18. The light pipe is not essential but affords flexibility in locating the chopper relative to the rest of the system. The light exits the light pipe into a spherical integrating cavity 20. The interior walls of the integrating cavity 20 reflect light impinging upon them diffusely, so that the light passes across the interior of the cavity 20 many times. The cavity 20 houses a cell 22 filled with low-pressure, high-purity oxygen.

Depending on the bandpass selected, the oxygen selectively absorbs wavelengths in the A-band or B-band. After the chopper 16 closes, the oxygen reemits some of the absorbed light as fluorescence. The light emitted by the oxygen is detected by a photomultiplier tube 24. The output from the photomultiplier tube 24 is processed by instrumentation 26 including a preamplifier and a discriminator and then interpreted by a data acquisition system 28 which is synchronized with chopper driver 30.

In general, the photomultiplier tube 24 is exposed to the full collected light when the chopper is open. This exposure would damage the photomultiplier tube 24 if its normal bias voltage were applied during that time. Therefore, the synchronization signal from the chopper driver 30 also is generally used by the bias controller 32 to remove the photomultiplier tube 24 bias voltage while the chopper 16 is open. Alternatively, the photomultiplier tube 24 may be shielded from the collected light by a second chopper 34 with driver 36 that is synchronized with driver 30 so that chopper 34 is closed whenever chopper 16 is open.

The use of integrating cavity 20 enhances the sensitivity of the invention in two aspects. It increases the fraction of collected light that is absorbed by the oxygen in the cell 22, and it also increases the fraction of the oxygen fluorescence that ultimately reaches the detector 24. The exact shape of the cavity 20 is not critical. However, a spherical shape has the lowest ratio of surface area to volume and thus offers the highest optical efficiency.

The pressure of the oxygen in the cell 22 and the chopper 16 speed cannot be chosen independently owing to the relation of both of these parameters to the time constant of the oxygen fluorescence. The oxygen A-band has a radiative lifetime of about twelve seconds. That is, in the absence of other mechanisms of energy loss, the absorption and reemission of a photon by an oxygen molecule would be separated, on average, by an elapsed time of twelve seconds. However, in most cases, the oxygen molecule will lose the absorbed energy as a result of collisions with other molecules, including other oxygen molecules. Thus, as the cell pressure is increased, the time constant of the oxygen fluorescence decay and the overall fluorescence efficiency decrease; however, under this circumstance there is also more oxygen in the cell to absorb light, so the net effect of the pressure increase is to leave the oxygen fluorescence intensity unchanged. Another consideration is that efficient detection requires that the chopper period be comparable to or shorter than the fluorescence lifetime. It is furthermore desirable to use as slow a chopper speed as possible. These two requirements dictate that the lowest feasible cell pressure be used. The cell pressure cannot be arbitrarily low, however, because at very low cell pressures the excited oxygen molecules can diffuse rapidly to the cell wall and lose their energy by collisions there. In practice, for a spherical cell of 4" diameter it is feasible to use a pressure of approximately 10 Torr, and thereby to achieve a fluorescence lifetime of about 35 milliseconds. Under these conditions a typical chopper frequency is 13 Hz.

Another factor that limits the fluorescence lifetime is quenching of the excited oxygen molecules by impurities in the oxygen, most of which are far more efficient quenchers than are other oxygen molecules. Of the likely oxygen contaminants, water vapor is the most detrimental to the performance of the invention, so the cell 22 also preferably contains a desiccant such as barium oxide or phosphorous pentoxide.

It will be appreciated that the presence in the system of any other fluorescent materials excitable by the collected light will degrade the performance of the spectral line discriminator as they will lack the spectral selectivity of the oxygen. In particular, most glasses can be excited to fluoresce by light having wavelengths in the 760 nm spectral range or shorter, with a fluorescence lifetime in the milliseconds range. Mineral fillers for adhesives also can behave in this way. The best nonfluorescent material for the oxygen cell 22 and photomultiplier tube 24 envelope is fused quartz, which is nonfluorescent and is compatible with the requirements for gas purity and dryness. Most plastics, including dyed plastic filters, are acceptable optically, in that any fluorescence they exhibit decays quickly (in <<1 millisecond) and thus does not interfere with the detection of the oxygen fluorescence.

When an oxygen molecule in the cell 22 absorbs a photon corresponding to a B-band wavelength, the excited molecule loses energy in collisions and within microseconds assumes the same state that a molecule assumes immediately after absorbing an A-band photon. Thereafter, the fluorescence from such a molecule is indistinguishable from that resulting from stimulation by A-band wavelengths. The fluorescence by the oxygen in the cell 22 is in the 760 nm region for either bandpass selection.

Thus, if the spectral line discriminator is intended to work only in the B-band region, a filter 38 may be interposed between the output of the integrating cavity 20 and the photomultiplier tube 24. Filter 38 absorbs light in the 680 nm region and transmits in the 760 nm region. Therefore the photomultiplier tube 24 is never exposed to the intense collected light, and it is not necessary to remove its bias voltage while the chopper 16 is open. Exposure of the photomultiplier tube 24 to B-band light is undesirable even with the voltage bias removed, because this can cause excess dark current when the bias is restored. This effect is seen in the cathode type customarily designated as S-20 and seems to be the result of the relatively higher energy of the B-band photons. In contrast, exposure of the photomultiplier tube 24 to A-band light in the absence of the bias voltage causes little or no increase in dark current, for the milliseconds time scale relevant here. However, exposure of the photomultiplier tube 24 to collected A-band light can excite fluorescence of the photomultiplier tube 24 envelope, if that is made of a fluorescent material.

The intensity of chlorophyll fluorescence at the A-band wavelength of 760 nm is typically about one-third of the peak fluorescence over its entire spectrum. Chlorophyll fluoresces more strongly at wavelengths in the B-band than in the A-band, with lower leaf reflectivity. However, the absorption by atmospheric oxygen is about fourteen times stronger in the A-band than in the B-band. The net result of these factors is that the spectral line discriminator will require only modestly longer observing time in B-band, as compared with A-band, to obtain a given signal-to-noise ratio; also, the ratio of chlorophyll fluorescence signal to residual response to reflected sunlight is comparable in both cases. This comparison between operation in the two bands, of course, depends to some extent on the species, health, etc.

of the plants being observed. One advantage of B-band operation is that there is less reabsorption of the plants' fluorescence by the air between the plant and the observer. In A-band, this reabsorption reduces the fluorescence signal to 50% of its initial value in approximately 200 feet, while for B-band the range is approximately 2500 feet. Even the shorter A-band range, however, is usable for many applications, such as irrigation control for crops.

It will therefore be seen that the foregoing represents a highly advantageous approach to detection of fluorescence from plants. The terms and expressions employed herein are used as terms of description and not of limitation, and there is no intention, in the use of such terms and expressions, of excluding any equivalents of the features shown and described or portions thereof, but it is recognized that various modifications are possible within the scope of the invention claimed.

What is claimed is:

1. A method of detecting fluorescence in the A-band or the B-band from a sunlit target, the method comprising the steps of:
   A. passing light comprising the A-band or B-band fluorescence into a cavity containing oxygen gas,
   B. periodically interrupting passage of the light into the cavity; and
   C. detecting fluorescence by the oxygen gas while the passage of the light into the cavity is interrupted so as to provide an output indicative of the fluorescence in said A-band or, B-band.

2. The method of claim 1 wherein a cell containing the oxygen gas is housed in the cavity.

3. The method of claim 2 wherein the cell is of fused quartz.

4. The method of claim 2 wherein the cell contains a desiccant.

5. The method of claim 1 wherein the cavity has an interior surface of high diffuse optical reflectivity.

6. The method of claim 1 wherein the cavity is spherical.

7. The method of claim 1 wherein the oxygen gas is at low pressure.

8. The method of claim 1 wherein the light makes a plurality of traverses through the oxygen gas.

9. The method of claim 1 further comprising the step of passing the light through a bandpass filter.

10. The method of claim 9 wherein the bandpass filter passes light in the A-band or the B-band.

11. The method of claim 1 wherein the fluorescence is detected by a photomultiplier tube.

12. The method of claim 11 wherein the photomultiplier tube has a bias voltage, the bias voltage being removed while light passes into the cavity.

13. The method of claim 1 further comprising the steps of:
    A. passing the light through a bandpass filter that passes light in the B-band but not in the A-band before passing the light into the cavity; and
    B. passing the fluorescence by the oxygen gas through a bandpass filter that passes light in the A-band but not in the B-band before detecting the fluorescence by the oxygen gas.

14. The method of claim 1 wherein the step of detecting fluorescence by the oxygen gas is interrupted while light passes into the cavity.

15. An apparatus for detecting fluorescence in the A-band or the B-band from a sunlit target, the apparatus, comprising:
    A. a cavity containing oxygen gas
    B. means for directing light from the target into the cavity;
    C. means for periodically interrupting light into the cavity; and
    D. a light detector positioned to sense fluorescence by the oxygen gas and there by provide an output indicative of the fluorescence in said A-band or B-band.

16. The apparatus of claim 15 wherein a cell containing the oxygen gas is housed in the cavity.

17. The apparatus of claim 16 wherein the cell contains a desiccant.

18. The apparatus of claim 16 wherein the cell is of fused quartz.

19. The apparatus of claim 15 wherein the cavity is spherical.

20. The apparatus of claim 15 wherein the cavity has an interior surface of high diffuse optical reflectivity.

21. The apparatus of claim 15 wherein the oxygen gas is at low pressure.

22. The apparatus of claim 15 wherein the detector is a photomultiplier tube.

23. The apparatus of claim 15 further comprising a light pipe.

24. The apparatus of claim 15 further comprising a means for periodically interrupting passage of light between the cavity and the detector.

25. The apparatus of claim 15 further comprising a bandpass filter.

26. The apparatus of claim 25 wherein the bandpass filter passes light in the A-band or the B-band.

27. The apparatus of claim 15 further comprising:
    A. a bandpass filter that passes light in the B-band but not in the A-band; and
    B. a bandpass filter that passes light in the A-band but not in the B-band.

28. The apparatus of claim 27 wherein the bandpass filter that passes light in the A-band but not in the B-band is interposed between the cavity and the detector.

29. The apparatus of claim 15 wherein the light detector has a bias voltage and further comprising a means for removing the bias voltage while the light into the cavity is interrupted.

30. The apparatus of claim 15 wherein radiation leaves the cavity and further comprising a means for periodically preventing the radiation leaving the cavity from entering the light detector.

* * * * *